United States Patent [19]

Farr

[11] Patent Number: 4,950,277

[45] Date of Patent: Aug. 21, 1990

[54] ATHERECTOMY CUTTING DEVICE WITH ECCENTRIC WIRE AND METHOD

[75] Inventor: Andrew F. Farr, Spring Valley, Calif.

[73] Assignee: InterVentional Technologies, Inc., San Diego, Calif.

[21] Appl. No.: 299,146

[22] Filed: Jan. 23, 1989

[51] Int. Cl.⁵ .................................................. A61D 1/02
[52] U.S. Cl. ..................................... 606/159; 606/180; 604/22; 604/27; 604/49; 604/53
[58] Field of Search ............... 606/106, 159, 170, 171, 606/180; 604/27, 35, 49, 52, 53, 22

[56] References Cited

U.S. PATENT DOCUMENTS

| | | | |
|---|---|---|---|
| 2,729,210 | 1/1956 | Spencer | 128/2 |
| 2,749,909 | 6/1956 | Ullery et al. | 128/2 |
| 3,512,519 | 5/1970 | Hall | 128/2 |
| 3,605,721 | 9/1971 | Hallac | 128/2 |
| 3,654,911 | 4/1972 | Loge | 606/180 |
| 3,815,604 | 6/1974 | O'Malley et al. | 128/305 |
| 3,990,453 | 11/1976 | Douvas et al. | 128/305 |
| 4,273,128 | 6/1981 | Lary | 128/305 |
| 4,320,762 | 3/1982 | Bentov | 128/343 |
| 4,441,509 | 4/1984 | Kotsifas et al. | 128/757 |
| 4,589,412 | 5/1986 | Kensey | 128/305 |
| 4,598,710 | 7/1986 | Kleinberg et al. | 128/318 |
| 4,610,662 | 9/1986 | Weikl et al. | 604/53 |
| 4,627,436 | 12/1986 | Leckrone | 128/303 |
| 4,631,052 | 12/1986 | Kensey | 604/22 |
| 4,636,195 | 1/1987 | Wolinsky | 604/53 |
| 4,640,296 | 2/1987 | Schnepp-Pesch et al. | 128/754 |
| 4,646,738 | 3/1987 | Trott | 128/305 |
| 4,653,496 | 3/1987 | Bundy et al. | 128/305 |
| 4,655,217 | 4/1987 | Reed | 128/305 |
| 4,655,771 | 4/1987 | Wallsten | 623/1 |
| 4,664,112 | 5/1987 | Kensey et al. | 128/341 |
| 4,665,918 | 5/1987 | Garza et al. | 128/343 |
| 4,669,469 | 6/1987 | Gifford, III et al. | 128/305 |
| 4,679,557 | 7/1987 | Opie et al. | 128/305 |
| 4,685,458 | 8/1987 | Leckrone | 128/303 |
| 4,686,892 | 8/1987 | Nash | 128/305 |
| 4,690,140 | 9/1987 | Mecca | 128/305 |
| 4,696,667 | 9/1987 | Masch | 604/22 |
| 4,708,147 | 11/1987 | Haaga | 128/753 |
| 4,728,319 | 3/1988 | Masch | 604/22 |
| 4,732,154 | 3/1988 | Shiber | 128/305 |
| 4,754,755 | 7/1988 | Husted | 128/305 |
| 4,757,826 | 7/1988 | Abdulhay | 128/757 |
| 4,765,332 | 8/1988 | Fischell | 128/305 |

OTHER PUBLICATIONS

Coronary Artery Incision and Dilation, B. G. Lary, M.D., Archieves of Surgery, Dec. 1980, vol. 115, pp. 1478–1480.

Method for Increasing the Diameter of Long Segments of the Coronary Artery, B. G. Lary, M.D., The American Surgeon, Jan. 1966, vol. 32, No. 1, pp. 33–35.

A Method for Creating a Coronary-Myocardial Artery, B. G. Lary, M.D., et al., Surgery, St. Louis, vol. 59, No. 6, pp. 1061–1064.

*Primary Examiner*—Mickey Yu
*Assistant Examiner*—Beth Anne Cicconi
*Attorney, Agent, or Firm*—Nydegger & Harshman

[57] ABSTRACT

An atherectomy cutting device for removing obstructive tissue from the lumen of a body vessel comprises a guide wire positionable in the lumen of the vessel, and a rotatable cutter supported on an eccentric wire. The eccentric wire has a distal portion extension establishing a substantially right angle with the eccentric wire and having a ring to permit sliding movement of the eccentric wire and cutter along the guide wire. The extension and eccentric wire also permit manipulative movement of the rotatable cutter in an arc around the guide wire. There is included a dual lumen sheath having a first lumen for supporting the guide wire and a second lumen for supporting the eccentric wire carrying the rotatable cutter.

Also included is a method for removing obstructive tissue which involves manipulating the eccentric wire about the guide wire to move the cutter in an arc about the guide wire and thus increase the portion of obstructive tissue contacted by the cutter.

14 Claims, 1 Drawing Sheet

ATHERECTOMY CUTTING DEVICE WITH ECCENTRIC WIRE AND METHOD

FIELD OF THE INVENTION

This invention relates generally to devices for removing obstructive tissue from body vessels, such as arteries. More particularly, this invention relates to an apparatus for operably positioning a cutter against obstructive tissue in the lumen of a vessel to remove the obstructive tissue. This invention is particularly, but not exclusively, useful for atherectomy and related procedures.

BACKGROUND OF THE INVENTION

In recent years, various means and procedures have been developed to clear or open occluded arteries and other body vessels in order to restore the necessary circulation of fluids such as blood, through the body. In many situations, such intravessel procedures are preferable to the so-called "bypass" operations because such procedures can be relatively quickly performed and do not require an incision into the chest cavity or some other part of the body. Consequently, various procedures and several different devices for performing these procedures have been developed.

In general, there are three ways to eliminate or ameliorate the difficulties caused by an occlusion in a body vessel. First, it may be possible to dissolve the obstructive tissue causing the occlusion by the ingestion or injection of properly selected medicaments. Such treatment, however, may be ineffective due to an excessive time for response, or undesirable due to adverse side effects. Second, well known angioplasty procedures utilizing a balloon catheter may be used to attempt to flatten the obstructive tissue against the vessel wall. With the angioplasty procedures, however, the obstructive tissue causing the occlusion remains in situ after the procedure is performed. Thus, the problem may be compromised but it is not eliminated and there remains the real probability there will be a restenosis. Third, atherectomy related procedures may be performed.

In any atherectomy procedure, the obstructive tissue causing the occlusion in the vessel (or at least a part of this obstructive tissue) is cut or clipped from the lumen of the vessel. As should be readily apparent, the instruments used for this purpose require specifically designed cutting devices. Further, the devices which are used for controlling the position of the cutting device in the lumen require special fabrication and design considerations. Specifically, both the cutting device itself and whatever control elements are inserted into the vessel with the cutting device must be miniaturized.

Several atherectomy related devices have been previously disclosed. Exemplary of such devices is U.S. Pat. No. 4,754,755 to Husted which discloses a catheter with a cylindrical rotary blade that is used to clear arterial obstructions. As another example of an atherectomy device, U.S. Pat. No. 4,732,154 to Shiber discloses a rotary catheter system for this same purpose. For each of the devices disclosed in these references, however, the effective cutting area of the blade of the device is limited. This is so because, in these typical devices, the cutting action of the rotating blade is not capable of extending beyond the periphery of the tubular structure which is used to introduce the blade into the vessel. Consequently, the effective cutting radius of the blade once inside the vessel is limited by the size of the opening used for an entry site. It usually happens, however, that the maximum permissible size of the opening for an entry site is smaller than the cross-sectional area of the vessel lumen at the location where the atherectomy cutter is to be operated. Thus, there is a need for a cutter which can be manipulated in the vessel to increase the effective area covered by the cutter.

The present invention recognizes the need for an atherectomy cutter whose area of effective cutting action can be extended, once it is positioned within the lumen of a body vessel, to increase the cutting effectiveness of the device. The present invention also recognizes the need to be able to operably position the cutting blades against the obstructive tissue. Further, the present invention recognizes the need for a cutter which can be manipulated to increase the scope of coverage attainable by an atherectomy cutter.

In light of the above, it is an object of the present invention to provide a cutter for an atherectomy device which can be manipulated to extend its area of coverage once it is inside the lumen of a body vessel. Another object of the present invention is to provide an atherectomy device which can be operatively positioned within the lumen as required to excise obstructive tissue from inside the lumen of a body vessel. Still another object of the present invention is to provide an atherectomy device which can be effectively controlled during the cutting of obstructive tissue from the inside of a body vessel. Yet another object of the present invention is to provide an atherectomy device which is easy to use, relatively easy to manufacture and comparatively cost effective.

SUMMARY OF THE INVENTION

An atherectomy cutting device for removing obstructive tissue from the lumen of a body vessel comprises a guide wire positionable in the lumen, and a rotatable cutter supported on an eccentric wire. The eccentric wire has a distal portion extension slidably engaged with the guide wire for moving the eccentric wire and the supported cutter along the guide wire. The distal portion extension of the eccentric wire establishes a substantially right angle with the eccentric wire and has a ring formed on the end of the extension to permit sliding movement of the eccentric wire along the guide wire. The extension also permits movement of the rotatable cutter in an arc around the guide wire.

In the preferred embodiment, there is included a dual lumen sheath having a first lumen for supporting the guide wire and a second lumen for supporting the eccentric wire which carries the rotatable cutter. There is also included a torque tube positioned about the eccentric wire and fixedly attached to the cutter for rotating the cutter. The rotatable cutter and torque tube are hollow and are attached together in fluid communication for connection with a suction mechanism for suctioning tissue clippings from the vessel through the torque tube. Also provided is a mechanism for steering the guide wire, as well as a mechanism for manipulating the eccentric wire. Thus, means are provided for controlling the operable position of the rotatable cutter.

There is also a method for removing obstructive tissue comprising the steps of inserting a guide wire into the vessel across the obstructive tissue; slidably engaging an eccentric wire with the guide wire for sliding movement of the eccentric wire along the guide wire; positioning a cutter on the eccentric wire to bring the cutter into contact with the obstructive tissue; rotating the cutter; and manipulating the eccentric wire to move the cutter in an arch about the guide wire. With this method, the portion of obstructive tissue contacted by the cutter is increased.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
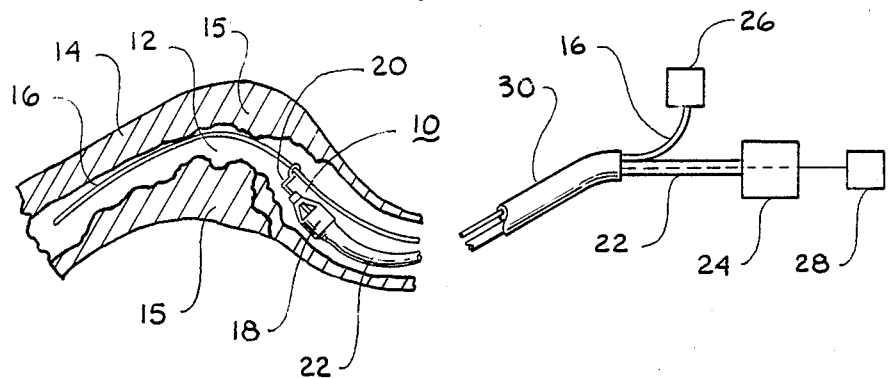
FIG. 1 is a side view, partly in cross section, of the atherectomy cutting device with eccentric wire being utilized in its intended environment in accordance with the present invention.

FIG. 1 shows the atherectomy cutting device, generally designated 10, with the eccentric wire of the present invention as it would be operably placed in its intended environment. More specifically, the cutting device 10 is shown positioned within the lumen 12 of a body vessel 14. The body vessel 14 may be an artery, a vein, a passageway, or any other vessel in the body having a lumen 12 therethrough. As shown, cutting device 10 utilizes aguide wire 16 which is positioned within lumen 12 of vessel 14 to guide and position a rotatable cutter 18 within the lumen 12. Specifically, rotatable cutter 18 is carried on an eccentric wire 20 which is slidably positioned along guide wire 16. For purposes of the present invention, the rotatable cutter 18 is rotated by a torque tube 22 that is fixedly attached thereto and is operatively engaged to a suction and drive means 24. The guide wire 16 can be operably connected to positioning means 26 and steered through the vessel 14. Independently, eccentric wire 20 is connected to control means 28 for manipulating eccentric wire 20 about the guide wire 16 in a manner to be further explained below. Together, guide wire 16 and torque tube 22 are carried within a dual lumen sheath 30 which adds stability to device 10 and assists in operably positioning the rotatable cutter 18. In FIG. 1, cutting device 10 is shown positioned near a site where there is obstructive tissue 15 that needs to be cut away. Obstructive tissue 15 can be plaque or some other unwanted material which is occluding or tending to occlude lumen 12 of vessel 14.

Figure 2:
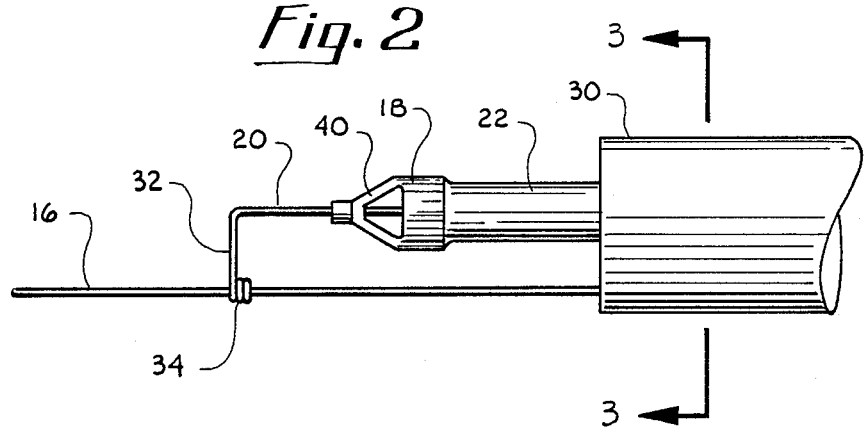
FIG. 2 is a side view of the atherectomy cutting device with eccentric wire in accordance with the present invention.

Referring now to FIG. 2, rotatable cutter 18 is shown rotatably mounted on eccentric wire 20. Rotatable cutter 18 may be of any of several configurations. Preferably, however, cutter 18 is of the type of atherectomy cutter disclosed and claimed in copending application Ser. No. 123,713 which was filed on Nov. 23, 1987 for an invention entitled "System for, and Method of, Excising Obstructive Tissue from Lumen of Living Beings" and assigned to the same assignee as the present invention. In any event, cutter 18 is connected in fluid communication with hollow torque tube 22. As seen in FIG. 2, eccentric wire 20 has a distal portion extension 32 for positioning the rotatable cutter 18 at a predetermined distance from guide wire 16. A ring 34 is formed at the end of distal portion 32 for slidable engagement along guide wire 16. In the embodiment shown, the distal portion extension 32 of eccentric wire 20 establishes a substantially right angle with the eccentric wire 20 for supporting the rotatable cutter 18 in an operable orientation at the desired distance from guide wire 16.

Figures 3, 4:
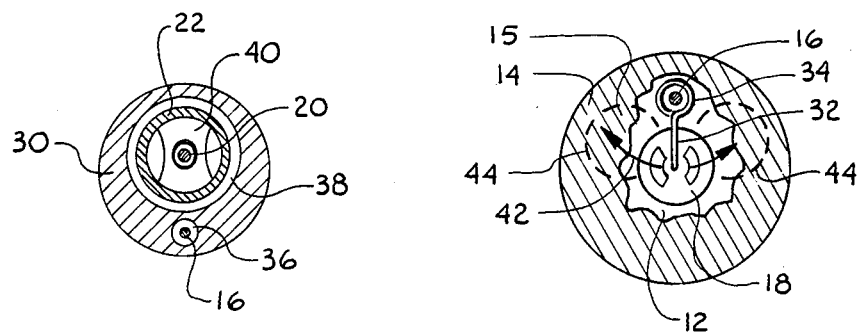
FIG. 3 is a cross-sectional view taken along line 3—3 of the atherectomy cutting device with eccentric wire as shown in FIG. 2.
FIG. 4 is a cross section of an obstructed body vessel with an end view of the atherectomy cutting device with eccentric wire being operably positioned therein in accordance with the present invention.

Referring now to FIG. 3, there is shown a cross-sectional view of a preferred embodiment of the present invention incorporating a dual lumen sheath 30, having a first lumen 36 and second lumen 38. First lumen 36 provides a channel through which guide wire 16 may be slidably inserted and second lumen 38 provides a channel for slidably receiving torque tube 22. The respective diameters of first lumen 36 and second lumen 38 are chosen to slidably accomodate guide wire 16 and torque tube 22 appropriately. In addition, the distance between the respective central axis of each first lumen 36 and second lumen 38 is preferably chosen to be substantially the same as the length of distal portion extension 32. In this manner, first lumen 36 and second lumen 38 respectively assist in supporting and maintaining the desired distance between guide wire 16 and eccentric wire 20. Such cooperation will become more apparent in the description of the operation of the present invention which follows.

OPERATION

In the operation of the atherectomy cutter device of the present invention, reference should be made primarily to FIG. 4 which shows a cross-sectional view of a body vessel 14 having obstructive tissue 15 which is to be cut away to open lumen 12. First, guide wire 16 is inserted into the vessel 14 of a patient through an entry site (not shown), and steered by positioning means 26 through the lumen 12 of vessel 14 and into contact with the obstructive tissue 15. The rotatable cutter 18 and the eccentric wire 20 supporting rotatable cutter 18 with its attached torque tube 22 are then introduced into vessel 14 through the same entry site. The eccentric wire 20 carrying rotatable cutter 18 is then guided along guide wire 16 via the sliding engagement of ring 34 of distal portion extension 32 with eccentric wire 20. Once rotatable cutter 18 has been guided to the site of obstructive tissue 15, the drive means 24 is activated to rotate torque tube 22 and rotatable cutter 18. The eccentric wire 20 can then be manipulated by the operator using control means 28 to move the rotating cutter 18 in an arc about guide wire 16j represented by arrow 42. This results in extending cutting area 44 for removal of greater quantities of obstructive tissue 15.

As can be appreciated, this operable positioning of cutter 18 effectively increases the cutting area of device 10 from that of the surface area of a cross section of rotating cutter 18 to the increased and extended cutting area 44 as shown in FIG. 4. As seen in FIG. 4, this can result in a significant increase in the area which can be cut through obstructive tissue 15. On the other hand, the entry site through which the atherectomy cutting device 10 is introduced into vessel 14 need not be enlarged and, instead, may be kept significantly smaller than the effective cutting area of device 10.

The cutting area, in accordance with the present invention, can thus be extended once the cutting device has been guided and manipulated into contact with obstructive tissue 15. Moreover, by properly manipulating the eccentric wire 20, cutter 18 can be selectively positioned against portions of obstructive tissue 15 on the inner wall of vessel 14.

Once the cutting procedure has begun, the clippings of obstructive tissue 15 and other debris generated by the cutting action can be removed from lumen 12 by the suction and drive means 24. This is accomplished by suctioning clippings into and through hollow rotatable cutter 18 and through hollow torque tube 22 away from the site of obstructive tissue 15. Again, positioning means 26 can be used to steer guide wire 16, and control means 28 can be used to manipulate eccentric wire 20, to bring the rotating cutter head into contact with the obstructive tissue as may be required.

While the particular atherectomy cutting device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A device for removing obstructive tissue from a lumen of a body vessel which comprises:
   a first wire positionable in said lumen;
   a second wire having a distal end slidably engaged with said first wire; and
   a rotatable cutter supported by said second wire for movement therewith along said first wire.

2. A device for removing obstructive tissue from the lumen of a body vessel as recited in claim 1 further comprising means for moving said cutter in an arc around said first wire.

3. A device for removing obstructive tissue from the lumen of a body vessel as recited in claim 1 further comprising a sheath having a first lumen for supporting said first wire and a second lumen for supporting said second wire.

4. A device for removing obstructive tissue from the lumen of a body vessel as recited in claim 1 wherein said distal end of said second wire is formed with a ring for slidable engagement along said first wire.

5. A device for removing obstructive tissue from the lumen of a body vessel as recited in claim 4 wherein said distal end of said second wire is bent to establish an extension oriented substantially perpendicular to said first wire.

6. An apparatus for operably positioning an atherectomy cutter against obstructive tissue in the lumen of an artery to remove clippings of the artery which comprises:
   an eccentric wire for supporting said cutter, said eccentric wire having a proximal end and a distal end;
   an extension attached to said distal end to establish a substantially right angle with said eccentric wire;
   a ring attached to said extension; and
   a guide wire positioned in said ring to permit sliding movement of said eccentric wire along said guide wire.

7. An apparatus for operably positioning an atherectomy cutter against obstructive tissue in the lumen of an artery to remove clippings of the artery as recited in claim 6 further comprising means for moving said cutter in an arc around said guide wire.

8. An apparatus for operably positioning an atherectomy cutter against obstructive tissue in the lumen of an artery to remove clippings of the artery as recited in claim 6 wherein said extension is integral with said eccentric wire.

9. An apparatus for operably positioning an atherectomy cutter against obstructive tissue in the lumen of an artery to remove clippings of the artery as recited in claim 6 further comprising a sheath having a first lumen for supporting said guide wire and a second lumen for supporting said eccentric wire.

10. An apparatus for operably positioning an atherectomy cutter against obstructive tissue in the lumen of an artery to remove clippings of the artery as recited in claim 6 further comprising torque means positioned over said eccentric wire and fixedly attached to said cutter for rotating said cutter.

11. An apparatus for operably positioning an atherectomy cutter against obstructive tissue in the lumen of an artery to remove clippings of the artery as recited in claim 10 wherein said torque means comprises a hollow tube.

12. An apparatus for operably positioning an atherectomy cutter against obstructive tissue in the lumen of an artery to remove clippings of the artery as recited in claim 11 further comprising suction means operatively connected to said torque means for removing clippings from the artery through said torque means.

13. An apparatus for operably positioning an atherectomy cutter against obstructive tissue in the lumen of an artery to remove clippings of the artery as recited in claim 6 wherein said guide wire is steerable.

14. A method for removing obstructive tissue from the lumen of a vessel which comprises the steps of:
   inserting a first wire into the vessel across the obstructive tissue;
   engaging an end of a second wire with said first wire for sliding movement of said end along said first wire;
   positioning a cutter on said second wire for movement of said cutter with said second wire along said first wire to bring said cutter into contact with the obstructive tissue;
   rotating said cutter to cut the obstructive tissue; and
   manipulating said second wire to move said cutter in an arc about said first wire to increase the portion of obstructive tissue contacted by said cutter.

* * * * *